United States Patent [19]

Nakagawa et al.

[11] Patent Number: 5,471,058
[45] Date of Patent: Nov. 28, 1995

[54] ANESTHESIA MONITOR

[75] Inventors: Kazuo Nakagawa; Yuichi Iritani; Hiromi Yamazaki; Yasushi Takakuwa, all of Tokyo, Japan

[73] Assignee: Nikkiso Co., Ltd., Tokyo, Japan

[21] Appl. No.: 9,798

[22] Filed: Jan. 27, 1993

[30] Foreign Application Priority Data

Jan. 27, 1992 [JP] Japan .................. 4-011916

[51] Int. Cl.$^6$ ................................. B01D 59/44
[52] U.S. Cl. ................. 250/291; 250/282; 250/292
[58] Field of Search .................. 250/291, 290, 250/281, 282, 292

[56] References Cited

U.S. PATENT DOCUMENTS

| | | | |
|---|---|---|---|
| 3,742,212 | 6/1973 | McIver, Jr. | 250/291 |
| 4,315,149 | 2/1982 | Ledford, Jr. | 250/291 |
| 4,535,235 | 8/1985 | McIver, Jr. | 250/291 |
| 4,761,545 | 8/1993 | Marshall et al. | 250/291 |
| 4,931,640 | 6/1990 | Marshall et al. | 250/292 |
| 4,945,234 | 7/1990 | Goodman et al. | 250/290 |
| 5,047,636 | 9/1991 | Farrar et al. | 250/291 |
| 5,070,245 | 12/1991 | Rantala et al. | 250/343 |
| 5,264,697 | 11/1993 | Nakagawa et al. | 250/291 |
| 5,301,537 | 4/1994 | Atkinson | 73/40 |

FOREIGN PATENT DOCUMENTS

| | | |
|---|---|---|
| 0515690A1 | 12/1992 | European Pat. Off. . |
| WO90/14687 | 11/1990 | WIPO . |

*Primary Examiner*—James Beyer
*Attorney, Agent, or Firm*—Davis Hoxie Faithfull & Hapgood

[57] ABSTRACT

The invention provides an anesthesia monitor being able to directly make a separation and a determination in real time all components of a gas in which components having the same integer molecular weight exists, more particularly an expiration gas and an inspiration gas as the object of analysis. The monitor has a small size, a low price and a operational facility. A microscopic quantity of the expiration gas is introduced from a circular route of an anesthesia circuit for an inhalation anesthesia to the anesthesia monitor through a material pipe-line. A gas portion is transmitted by a rotary pump through valves and opening and closing valves to a measurement cell within a vacuum chamber arranged in a gap of between magnetic poles of permanent magnets in a Fourier transformation mass analyzer so that the expiration gas is subjected to a high speed sampling. An ionization of the ions is carried out within the measurement cell. A cyclotron resonance is caused thereby causing a high frequency voltage which is received by receiving electrodes of the cell. After a digiterzation of the signals, a computer executes a Fourier transformation mass analyzing process.

12 Claims, 4 Drawing Sheets

ANESTHESIA MONITOR

BACKGROUND OF THE INVENTION

The invention relates to an anesthesia monitor, and more particularly to an anesthesia monitor for analyzing continuously a part of the inspiration and expiration of a living body so as to perform movement analyses about the respiration, the circulation and the metabolism thereof.

Such anesthesia monitors analyze concentrations of $N_2$, $O_2$, CO, $CO_2$, $N_2O$ and added anesthetics involved in the inspiration or expiration of a patient in order to keep well, i.e., satisfactory, the patient's condition. Normally, an inhalation anesthesia employs nitrous oxide ($N_2O$). Further, anesthetics such as halothane in which a hydrogen atom of alkane or ether is substituted by a halogen atom are recently employed. Thus, the variety of anesthetics used is increasing. It is required to perform the concentration analyses of such anesthetics comprising many components. The conventional anesthesia monitors have normally utilized an infrared spectroscopy or a mass spectrometry as a analysis method of the anesthetic concentration involved in the expiration or the inspiration. The mass spectrometry usually employs a uni-convergence method or a quadruple-pole method to analyze the expiration or the inspiration.

As described above, since the variety of anesthetics tends to be increased, the anesthesia monitor is required to possess the following performance characteristics. First, one requirement is that the anesthesia monitor is able to make a measurement of various components involved in the expiration and the inspiration of the patient. Second, one requirement is that the anesthesia monitor is able to make a separation and a determination of components which have analogous properties to one another. Third, one requirement is that the anesthesia monitor is able to make a measurement of many components in real time. Fourth, one requirement is that the anesthesia monitor has a suitable size for an operation room, and in addition and ease of installation and operation thereof.

It will be investigated whether or not the above and prior known analyzing methods of the concentration comply with the above requirements.

The infrared spectroscopy has the following problems in a separation of the concentration of mixed gases. A first problem is that there exist many components of gases whose absorption spectrums overlaps with one another. For example, with respect to $N_2O$ and $CO_2$ being important as analyzing objects, $N_2O$ has an intensive spectrum peak in the range of the wavelength from 4.4 micrometers to 4.6 micrometers. In contrast, $CO_2$ has an intensive spectrum peak in the range of the wavelength from 4.2 micrometers to 4.4 micrometers. Thus, the intensive spectrum peaks of $N_2O$ and $CO_2$ overlap with one another in the vicinity of a wavelength of 4.4 micrometers. A normal anesthesia performed on condition of a high concentration of $N_2O$ and a low concentration of $CO_2$ forces the measurement results to have an error. A second problem is that the molecular collision causes a spectral line to be broad. In mixed gases, molecules of gas as a measuring object makes collisions with other molecules thereby causing an interchange of molecular energies. The molecular energy is varied according to the molecular weight and the dipole moment of the collision gas. As a result, the infrared absorption band becomes broad and the dummy absorption wavelength is also influenced. Thus, an error in the measurement results appears depending upon the circumstances of other components in the mixed gases. The third problem is that it is frequently difficult to make a measurement of halide anesthetics which are recently developed. The halide anesthetics have intensive absorption lines in the vicinity of a wavelength of 3.1 micrometers respectively. This makes it impossible to distinguish individuals of the halide anesthetics. A fourth problem is that the infrared spectroscopy is unable to make a measurement of components which are subjected to no variation of its dipole moments by a molecular oscillation such as a diatomic molecule. Thus, it is impossible to measure $N_2O$ and $CO_2$ and the like as serving basic components on an artificial respiration.

The mass spectrometry has the following problems. It is difficult to make a separation measurement of the component of any gases as measuring objects. Foe example, nitrous oxide ($N_2O$) which is frequently used for a general anesthesia has a molecular weight of 44.001. Carbon dioxide ($CO_2$) which frequently becomes an analyzing object for the respiration analysis has a molecular weight of 43.990. Both molecules have the same integer mass number. The difference in the precise mass number thereof is only 0.11 amu. The accomplishment of a direct separation determination of the above molecule components by measuring their molecular peaks thus requires a resolution of much more 10000. The resolution is defined by $$\text{Resolution} \gg \text{mass number}/(\text{peak interval}/2) = 8000.$$

The conventional mass spectrometry utilizing the mono-convergence system or the quadruple-pole system has a resolution of only approximately 1000. Thus, it is difficult to make directly the separation measurement. As a result, the conventional anesthesia monitor unwillingly uses the following methods.

In a first method, fragment peaks of all components expected to be involved in the mixed gases are compared, after which peaks, or uni-peaks which do not overlap with one another are selected. The height of the selected peak is regarded as a quantity of a component of the above mixed gases.

There exists a second method utilizing a multiple regression method which solves simultaneous equations or normal equations by the least square method. In the simultaneous equations, patterns coefficients of all components expected to be involved in the mixed gases are so utilized that unknown variables are the concentrations of the above components.

With respect to the first method, the separation measurements of $N_2O$ and $CO_2$ are unable to use molecular peaks having maximum intensity respectively. The separation measurement of $N_2O$ uses a fragment peak of M/z 30. The separation measurement of $CO_2$ uses a fragment peak of M/z 12. As is well known, such fragment peaks have an intensity that are considerably lower than that of the molecular peaks as base peaks. This causes the accuracy of the measurement to be lowered.

With respect to the second method, as it is known, when there exists an unexpected component in a material gas or a ratio of measurement peak signal to a noise is not sufficiently large, an unexpected large error occurs.

Further, there exists a gas chromatograph mass spectrometry method. In this method, the gas chromatograph used for the normal organic analyses are as previously prepared. The components of the mixed gases are separated according to specific holding times, followed by the mass analysis. Since such method has an analyzing period in the range from several minutes to several ten minutes, the above mentioned real time measuring condition is not satisfied and thus the method is not applicable to the patient expiration gas measurement application.

In addition, there exists a Fourier transformation mass spectrometer that is commercially available. The applicability of the method to the patient gas expiration and inspiration analyses is disclosed in Anal. Chem. 60, pp. 341–344, 1988. Disclosed therein is a large and extremely expensive apparatus utilizing a super-conductance magnet, which have not been applied to a general clinical application.

Furthermore, there exists a large bi-convergence mass spectrometer possessing a resolution more than $10^4$. Although such spectrometer is capable of making the separation measurement of $N_2O$ and $CO_2$ by using those molecular peaks, that is practically unsuitable for the anesthesia monitoring in that it has a large installation area (footprint), a complicated manner of operations, a long measuring time at a high resolution. The high price thereof also is bar to its application in a patient anesthesia monitoring application.

SUMMARY OF THE INVENTION

Accordingly, it is a primary object of the present invention to provide an improved anesthesia monitor using mass spectrometry.

It is a further object of the present invention to provide an anesthesia monitor using mass spectrometry utilizing a Fourier transformation ion cyclotron resonance of patient expiration and inspiration gas ions caused by a magnetic field provided by a permanent magnet in which analyzing objects includes components having equivalent integer molecular weights, which exist in the expiration gases and the inspiration.

It is a still further object of the present invention to provide an anesthesia monitor capable of making directly a separation and a determination of all gas components in real time.

It is a yet a further object of the present invention to provide an anesthesia monitor having a small size, a low price and a facility (simplicity) in its operation.

The above and other objects, features and advantages of the present invention will be apparent from the following descriptions.

An anesthesia monitor according to the present invention comprises a first unit for introducing mixed gases used for anesthesia or patient expirations into a measurement cell within a high vacuum chamber arranged between a gap of magnetic poles of permanent magnets and a second unit for applying, shortly after an ionization of introduced gases, high frequency voltages to irradiation electrodes constructing a part of the cell to cause an ion cyclotron resonance, and for making a detection and amplification of a high frequency signal voltage caused at receiving electrodes constructing a part of the cell, and for converting the signal into digital signals and for storing the digital signals in a memory of a computer, and for executing a Fourier transform process for stored digital signals to obtaining mass spectrums of the introduced gases, so as to perform a separation and determination for each component of the introduced gases.

According to the anesthesia monitor of the present invention, the mixed gases which includes an anesthetic is ionized within the measurement cell of the high vacuum chamber. The ionized ions are subjected to a high frequency voltage so as to cause a cyclotron resonance. The cyclotron resonance causes a high frequency voltage which is received (detected) by the receiving electrodes of the cell. The received signals are amplified and then converted Into digital signals. The digital signals are subjected to a Fourier transformation mass analyzing process by the computer so as to make the separation and determination measurements of the mixed gases in a real time.

BRIEF DESCRIPTION OF THE DRAWINGS

A preferred embodiment of the present invention will hereinafter fully be described in detail with reference to the accompanying drawings.

PREFERRED EMBODIMENTS OF THE INVENTION

Figure 2:
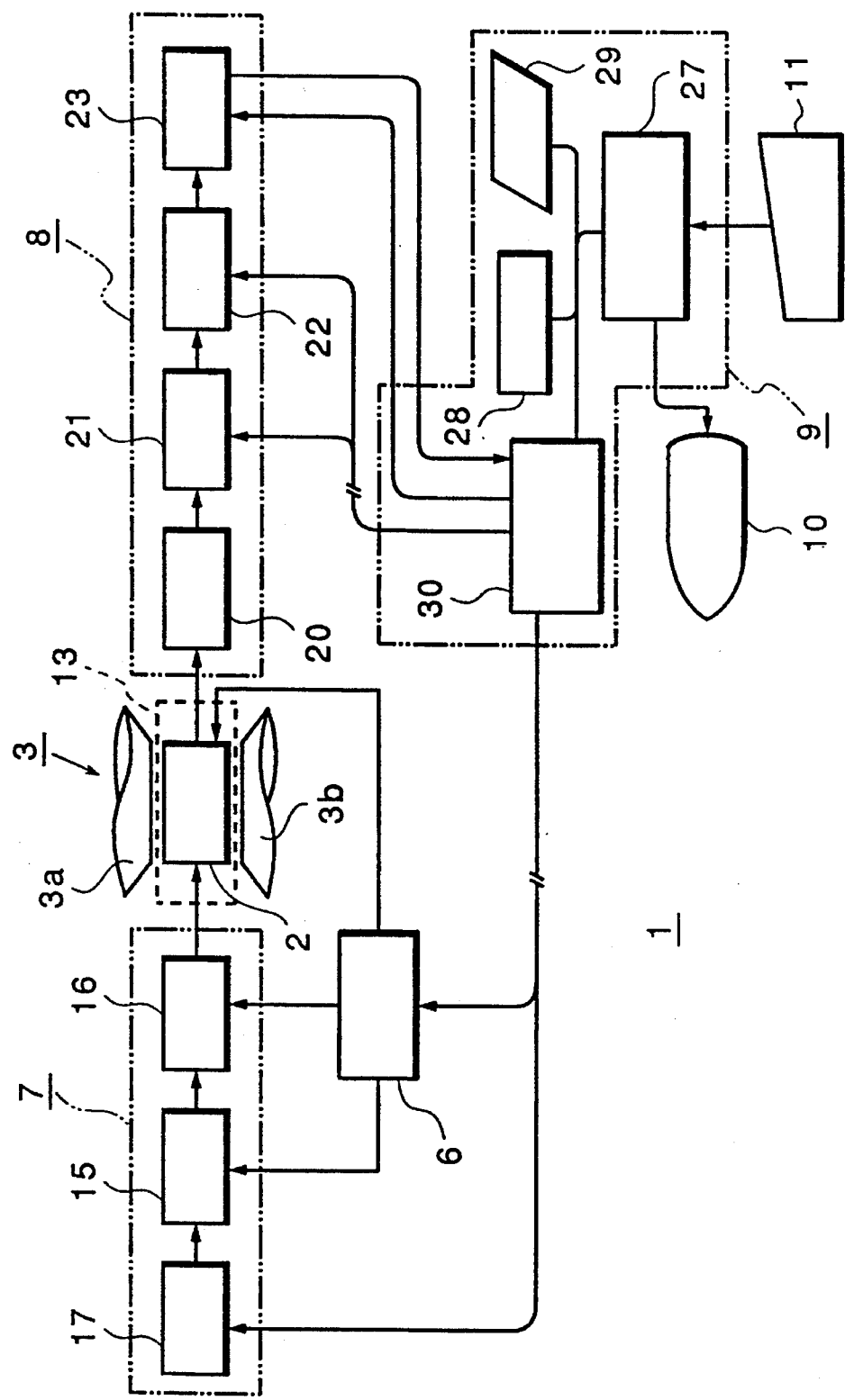
FIG. 2 is a block diagram illustrative of a structure of a Fourier transformation mass analyzing unit as a main unit of an anesthesia monitor of the present invention.

The measurement of an anesthesia monitor of the present invention utilizes a Fourier transformation mass analyzing method. In FIG. 2, the Fourier transformation mass analyzer 1 comprises a high vacuum cell 2, a permanent magnet 3, pulse control circuits 6 including an emission controller, a high frequency transmitter 7, a resonance signal detector 8, an arithmetic controller 9, a key board 11 and a CRT display 10. The high frequency transmitter 7 also comprises a clock generator 17, a high frequency oscillator 15 and a high frequency transmitter 16. The high frequency transmitter 7 transmits its output to the high vacuum cell 2.

The resonance signal detector 8 comprises a preamplifier 20 having as an input the measurement signals of the high vacuum cell 2, a high frequency amplifier 21, a low pass filter 22 and an analog to digital converter 23 for converting the detected signals to digital signals. The digital data of the measurement signals is transmitted to the arithmetic controller 9. The arithmetic controller 9 comprises a computer 27, a memory 28, an output unit 29 and an interface 30. The computer 27 is connected to a key board 11 and a CRT display 10 so as to control the pulse control circuits 6, the high frequency amplifier 21 and the low pass filter 22. The output of the pulse control circuits 6 is transmitted to the high frequency generator 15, the high frequency transmitter 16 and the high vacuum cell 2. The high vacuum cell 2 is protected by a super-high vacuum chamber 13 and accommodated within a constant temperature bath which is not illustrated.

Available as the high vacuum cell 2 is a cubic cell which comprises a pair of electrodes perpendicular to a direction of a magnetic field provided by the permanent magnet 3, a pair of irradiation electrodes parallel to the direction of the magnetic field, both of which are perpendicular to one another and a pair of receiving electrodes. An example of usable cubic cells is disclosed in R. T. McIver Jr. Rev. Sci. Instrum., 41, p. 555, 1970.

Figure 3:
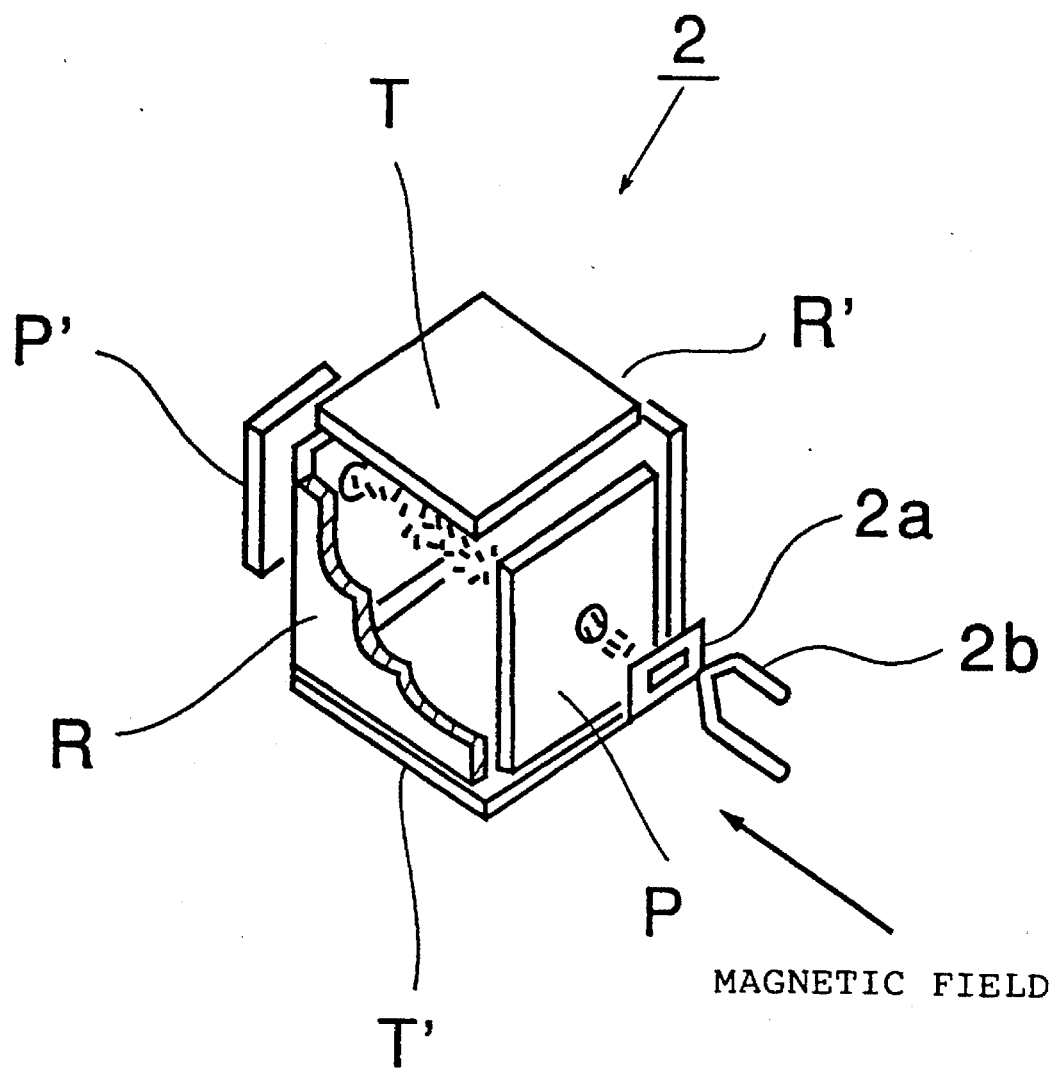
FIG. 3 is a schematic perspective view illustrative of a cubic cell as a high vacuum cell used in a Fourier transformation mass analyzing unit.

In FIG. 3, with respect to the cubic cell 2, a pair of electrodes P and P' are so arranged that the magnetic field of the permanent magnet 3 across the electrodes P and P' is at a right angle. The electrodes P and P' are connected to an insignificant positive potential, for example, 0.1 to 2 volts in order to prevent ions within the high vacuum cell 2 from drifting in the magnetic field direction. The irradiation electrodes T and T' are arranged between the electrodes P and P' so as to be parallel to the magnetic field and to face one another. Ions generated within the cubic cell 2 are applied in a short time, for example, 0.1 to 10 ms to high frequency signals from high frequency transmitter 7 so as to excite a cyclotron resonance. The receiving electrodes R and R' are arranged in parallel to the magnetic field so as to face one another and to be perpendicular to both of the electrodes T and T' and the electrodes P and P'. The receiving electrodes R and R' receive a high frequency signal voltage caused by the cyclotron resonance. The received high frequency signals are amplified by the preamplifier 20 and the high frequency amplifier 21, both of which exist within the resonance signal detector 8. After that, the amplified signals are transmitted through the low pass filter 22 to the analog to digital converter 23 and converted into digital signals. The digital signals are transmitted to the arithmetic controller 9. The arithmetic controller 9 stores the digital signals in the memory 28, after which the computer 27 executes the Fourier transformation mass analyzing process by using the stored data. The above ionization operation uses a grid 2a and a filament 2b.

The constant temperature bath as an additional unit prevents a temperature at the magnetic field of the permanent magnet 3 to be varied by the variation of the circumferential temperature. The permanent magnet 3 is provided with a pair of magnets facing one another so as to sandwich the high vacuum cell 2, The present invention is characterized in that the permanent magnet 3 is used for the Fourier transformation mass analyzer 1.

On the other hand, when a super-conductance magnet is used, the stability of the magnetic field is very high. Although the mass spectrum is subjected to neither a variation of the temperature nor a secular change, a large apparatus is very expensive as described above.

In contrast, when the permanent magnet or an electromagnet is used, the magnetic field is varied by a circumstantial temperature. The electromagnet and an alkali-magnet have temperature coefficients of approximately $-2\times10^{-4}/°C$. and $-2\times10^{-3}/°C$. respectively. To secure a resolution in the range from $10^4$ to $10^5$, it is required to compensate the variation of the magnetic field depending upon the temperature and the like. The method of compensating the variation of the magnetic field caused by the temperature variation is disclosed in PCT/JP91/01581.

Figure 1:
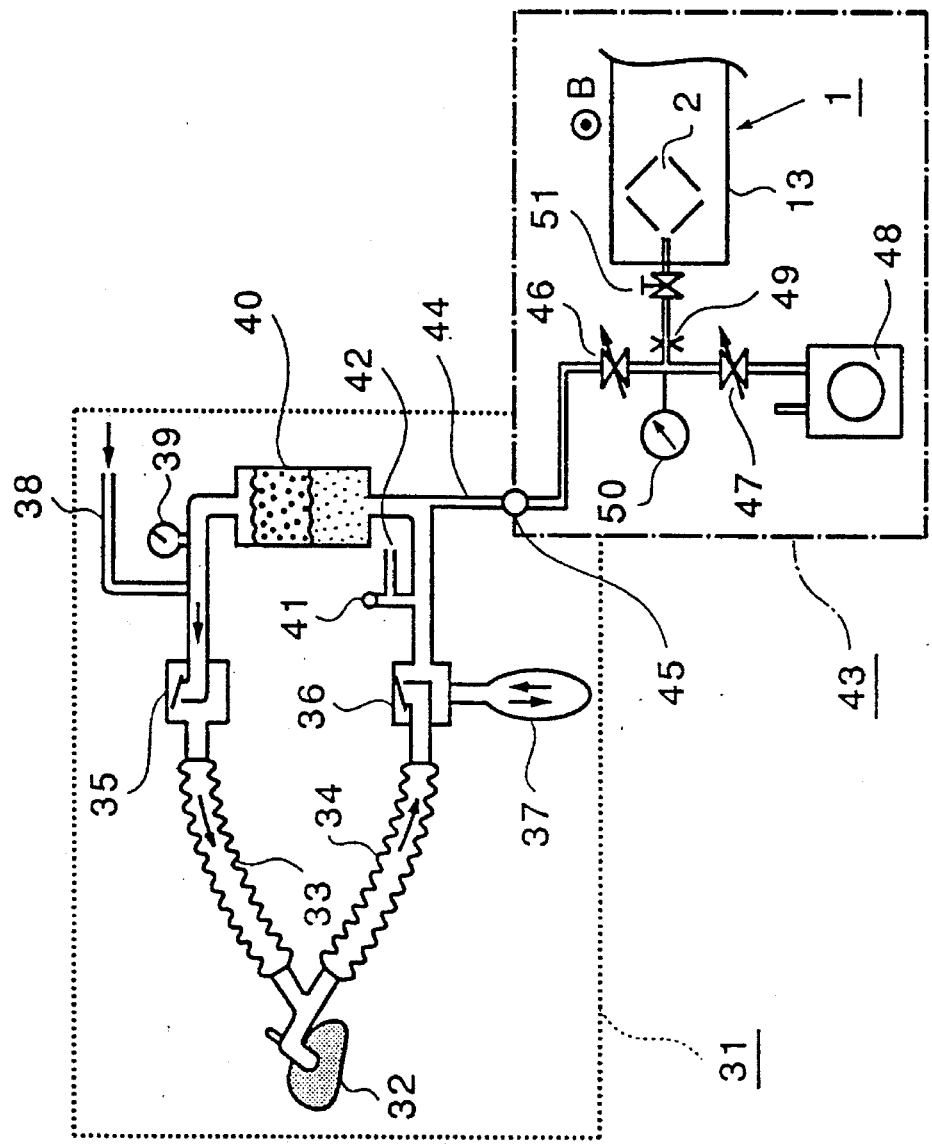
FIG. 1 is a block diagram illustrative of an anesthesia monitor and anesthesia circuits of the present invention.

In FIG. 1, commercially available anesthesia circuits encompassed by a dotted line 31 performs the inhalation anesthesia. The anesthesia monitor is encompassed by a broken line 43. The Fourier transformation mass analyzer 1 is illustrated but only its gas inlet port.

The anesthesia circuits 31 is connected through a gas inlet valve 35 transmitted from an airline 38 and through a coil 33 to a mask on an anesthesia patient. The expiration gas of a patient is transmitted through the coil 34 and through an outlet valve provided with a bag 37 to a carbon dioxide gas absorption unit 40 such as a canister, in addition, to an end connection 42 of a discharge unit for discharging unnecessary gas. A gas circulation route is so formed. The anesthesia circuits are further provided with an internal pressure gauge 39 for measuring a gas pressure within the circuits and a pop-off valve 41 at a branched portion to the end connection 42.

A part of the expiration gas is transmitted through the gas circulation route of the anesthesia circuits 31 to the anesthesia monitor 43. The gas portion is transmitted through a variable valve 46 existing at a side of a pile-line inlet port 45 and a variable valve 47 existing at an inlet port of a rotary pump 48 so that a microscopic (e.g., microliters) amount of the expiration gas is subjected to a high speed sampling. For the measurement cell 2 of the Fourier transformation mass analyzer 1, the pressure matching between the introduction gas pressure of approximately 1 to $1\times10^{-2}$ Torr and the measurement pressure of approximately $1\times10^{-7}$ to $1\times10^{-9}$ of the Fourier transformation mass analyzer 1 is performed by an orifice 49.

The measurement pressure is adjustable by the variable valves 46 and 47. Thus, when the variable valve 46 is closed and the variable valve 47 is opened, a quantity of the introduced gas portion is reduced. In contrast, when the variable valve 46 is opened and the variable valve 47 is closed, a quantity of gas introduced into the measurement cell 2 within The vacuum chamber 13 is increased. The measurement pressure of the Fourier transformation mass analyzer 1 is controlled so as to be suitable in the above mentioned range. The values of the measurement pressure is indicated by a vacuum gauge 50. The anesthesia monitor 43 involves an opening and closing valve 51. The mark "B" indicates a direction of the magnetic field.

Figure 4:
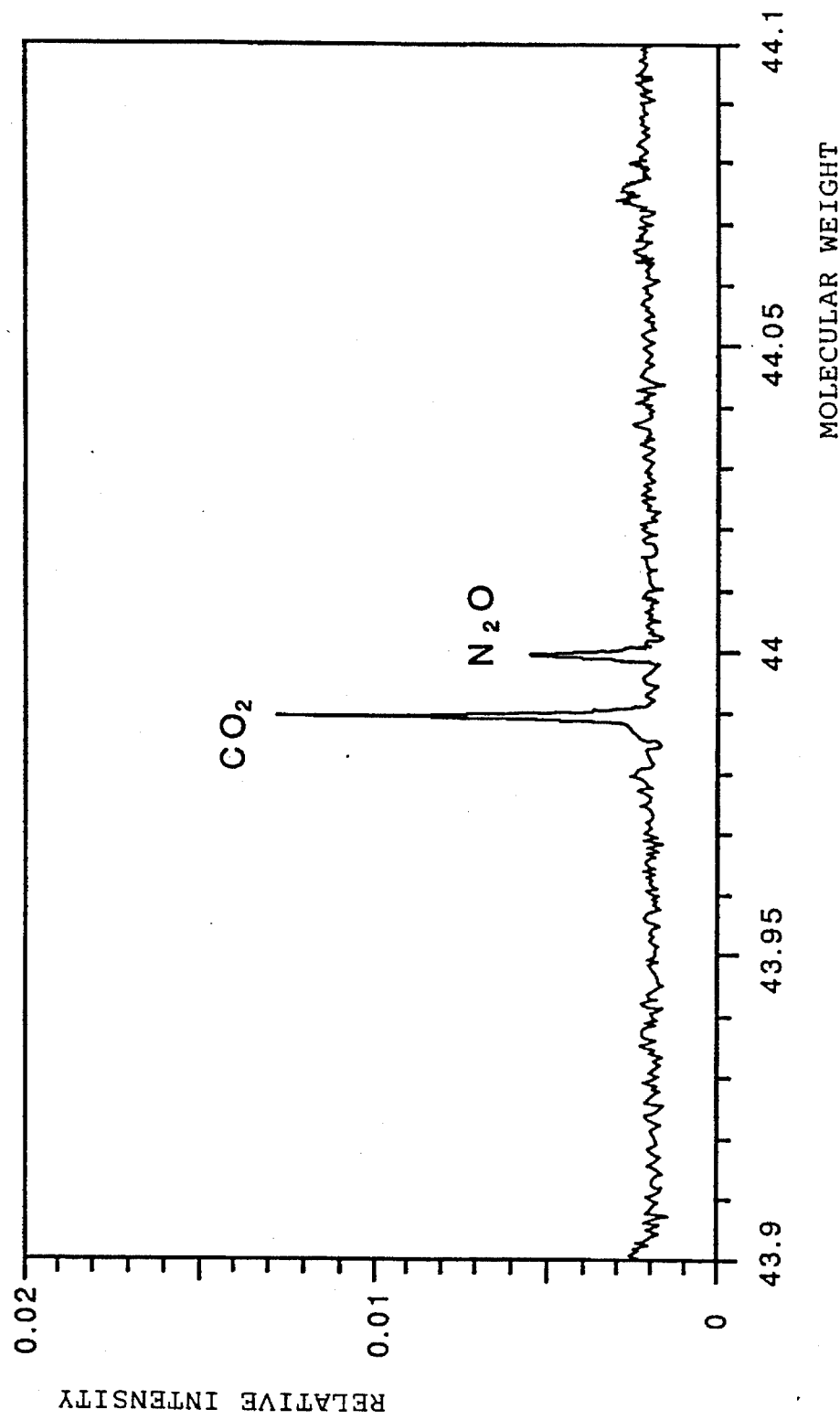
FIG. 4 is a view illustrative of a result of a measurement of components of $N_2O$ and $CO_2$ in a mixed gas.

In FIG. 4, a vertical axis indicates a relative intensity and a lateral axis indicates a molecular weight. As described above, although carbon dioxide and nitrous oxide have near molecular weights respectively, it is understood that the above components are so measured as to be separated from one another. Since each area ratio of the peaks of both the relative intensities is proportional to concentration of the each component, the concentrations of the components are defined by finding the peak area ratio. Analogous measurements are applicable to a measurement of nitrogen and carbon mono-oxide. The separation measurement of important components involved in the expiration gas and the inspiration gas of the living body is this performed in the real time. Since it is possible to separate $N_2O$ and $CO_2$, the anesthesia monitor serving for the general inhalation anesthesia is able to perform the recognition of a suitable ventilation, diagnoses of an air embolism and a shock and the like in the real time.

As described above, the anesthesia monitor according to the present invention employs a mass analysis utilizing the Fourier transformation ion cyclotron resonance of the expiration and inspiration ions by the magnetic field of the permanent magnet. The anesthesia monitor directly makes in the real time the separation and the determination of all components existing in the expiration and the inspiration gases as the analyzing objects in which there exist components having the same integer molecular weight.

Whereas modifications of the present invention will no doubt be apparent to a person of ordinary skill in the art, it is to be understood that the embodiments shown and described by way of illustration are by no means intended to be considered in a limiting sense. Accordingly, it is to be intended by the claims to cover all modifications of the invention which fall within the sprit and scope of the invention.

What is claimed is:

1. An anesthesia monitor comprising:
   a pair of permanent magnets having a gap therebetween and a steady state magnetic field in said gap;
   a measurement cell having pair of receiving electrodes, a pair of irradiation electrodes and a vacuum chamber exposed to said pairs of receiving and irradiation electrodes, the measurement cell being disposed in said gap and exposed to said steady state magnetic field;

a temperature bath associated with said pair permanent magnets to keep constant the temperature of the permanent magnets and maintain constant the steady state magnetic field;

means for introducing a gas sample including a first component and an anesthetic component into the measurement cell vacuum chamber;

an ion source to ionize said introduced gas sample components in said measurement cell;

means for applying a high frequency voltage to the irradiation electrodes after ionization of said introduced gas components to cause a cyclotron resonance of said ions in said vacuum chamber;

means for making a detection and amplification of a high frequency signal voltage caused by said resonance at said receiving electrodes;

means for converting said detected and amplified signal into a digital signal;

means for storing said digital signals in a memory;

means for executing a Fourier transformation process on said stored digital signals to obtain a mass spectrum of said introduced gas sample to perform a separation and a determination of each component of said introduced gas sample.

2. The anesthesia monitor as claimed in claim 1, wherein said means for applying the high frequency voltage comprises a clock generator, a high frequency oscillator and a high frequency transmitter.

3. The anesthesia monitor as claimed in claim 1, wherein said means for making the detection and amplification comprises receiving electrodes, a preamplifier, a high frequency amplifier and a low pass filter.

4. The anesthesia monitor as claimed in claim 1, wherein said means for converting the detected and amplified signals comprises an analog to digital converter.

5. The anesthesia monitor as claimed in claim 1, wherein said means for storing the digital data comprises a memory device of a computer.

6. The anesthesia monitor as claimed in claim 1, wherein said means for executing the Fourier transformation process comprises a computer.

7. The anesthesia monitor as claimed in claim 1 wherein:

said means for applying the high frequency voltage comprises a clock generator, a high frequency oscillator and a high frequency transmitter;

said means for making the detection and amplification comprises receiving electrodes, a preamplifier, a high frequency amplifier and a low pass filter;

said means for converting the detected and amplified signal comprises an analog to digital converter;

said means for storing the digital data comprises a memory device of a computer; and said means for executing the Fourier transformation process comprises a computer.

8. The anesthesia monitor as claimed in claim 1, wherein said means for introducing a gas sample further comprises:

an anesthesia gas flow circuit containing said gas sample at a pressure in a range of from $10^{-2}$ to 1 Torr;

a first airflow coupled to said anesthesia flow circuit having a first variable valve, a second variable valve and a pump, the pump being operable to cause a portion of said gas sample from said anesthesia gas flow circuit to flow through said first airline;

a second airline connected to said first airline at a location between the first and second variable valves, the second airline including an orifice and a valve, said valve being operable between an open condition for introducing a volume of said portion of gas supply in the first airline to said measurement cell vacuum chamber, and a closed condition, wherein the first and second variable valves are adjusted and the valve is operated to select said volume of gas sample and to deliver said volume through the orifice to the measurement cell vacuum chamber at a pressure in the vacuum chamber in the range of $10^{-7}$ to $10^{-9}$ Torrs.

9. A method for determining the components of a mixed gas including a first component and an anesthetic component comprising:

providing a vacuum chamber containing a measurement cell arranged in a gap between a first permanent magnet and a second permanent magnet having a steady state magnetic field therebetween;

maintaining said first and second permanent magnets at a constant termperature to minimize variations of said steady state magnetic field due to temperature changes;

providing the cell with irradiation electrodes and receiving electrodes;

introducing a mixed gas sample including the first and anesthetic components into the measurement cell and causing ionization of the introduced gas sample;

applying a high frequency voltage to the irradiation electrodes to cause a cyclotron resonance of said ions;

sensing a high frequency signal voltage caused by said resonance at the receiving electrodes;

converting said sensed signals into digital signals;

storing said digital signals;

executing a Fourier transformation process on said stored digital signals to obtain a mass spectrum of said introduced gas sample; and performing a separation and a determination of each of said first and anesthetic components of said introduced gas sample based on the mass spectrum.

10. The method of claim 9 further comprising providing the cell with a pair of electrodes and applying a voltage of from 0.1 to 2.0 volts to the electrodes to minimize drift of the ions in the magnetic field.

11. The method of claim 9 wherein the step maintaining said permanent magnets at the constant temperature further comprises maintaining the temperature of the measurement cell constant.

12. The method of claim 9 wherein the step of introducing a gas sample further comprises flowing the gas sample in a first flow circuit at a pressure in the range of from $10^{-2}$ to 1 Torr, extracting a portion of said gas sample in a first airline using a pump and a first and second variable valves to control the flow through the first airline, extracting a sample volume from the first airline using a second airline and a valve, passing the sample volume through an orifice in the second airline and into the measurement cell vacuum chamber, the orifice operating to reduce the pressure of the sample volume in the measurement cell to a pressure on the order of $10^{-7}$ to $10^{-9}$ Torr.

* * * * *

UNITED STATES PATENT AND TRADEMARK OFFICE
CERTIFICATE OF CORRECTION

PATENT NO. : 5,471,058
DATED : November 28, 1995
INVENTOR(S) : K. Nakagawa

It is certified that error appears in the above-indentified patent and that said Letters Patent is hereby corrected as shown below:

Column 3, line 67 delete "Into" and insert --into--;

Column 5, line 5 delete "applied" and insert --exposed for--;

Column 6, line 17 delete "The" and insert --the--;

Column 6, line 30, after "to" insert --the--;

Column 6, line 31, after "," delete "the";

Column 6, line 37 after "is" insert --thus--;

Abstract, line 13 after "gap" delete "of"; and

Abstract, line 19 delete "digiterzation" and insert --digitization--.

Signed and Sealed this

Fourteenth Day of October, 1997

Attest:

BRUCE LEHMAN

Attesting Officer

Commissioner of Patents and Trademarks